United States Patent [19]

Levine et al.

[11] 4,170,995

[45] Oct. 16, 1979

[54] CATHETER CLAMP

[76] Inventors: Robert A. Levine, 31 Pilgrim La., Guilford, Conn. 06437; Stephen C. Wardlaw, 128 Sunset Hill Dr., Branford, Conn. 06405

[21] Appl. No.: 853,321

[22] Filed: Nov. 21, 1977

[51] Int. Cl.² .............................................. A61B 17/00
[52] U.S. Cl. ............................... 128/346; 248/205 A; 24/73 A; 24/73 AP
[58] Field of Search ............... 128/349, 346, DIG. 26, 128/337; 248/205 A, 316 B; 24/73 AP, 73 A, 73 PB, 255 R, 257, 263

[56] References Cited

U.S. PATENT DOCUMENTS

| | | | |
|---|---|---|---|
| 2,590,006 | 3/1952 | Gordon | 128/206 |
| 3,601,127 | 8/1971 | Finegold | 128/346 X |
| 3,677,250 | 7/1972 | Thomas | 128/348 |
| 3,682,180 | 8/1972 | McFarlane | 128/DIG. 26 |
| 3,726,280 | 4/1973 | Lacount | 128/349 R |
| 3,760,811 | 9/1973 | Andrew | 128/DIG. 26 |
| 3,766,925 | 10/1973 | Rubricius | 128/346 |
| 3,782,388 | 1/1974 | Page | 128/348 |
| 3,990,454 | 11/1976 | Schlesinger | 128/349 R |
| 4,025,015 | 5/1977 | Kolic | 128/DIG. 26 |

OTHER PUBLICATIONS

"An Adjustable Spring Clamp for Cardiovascular Surgery" Nabatoff, Annals of Surgery, Aug. 1953, pp. 285-286.

Primary Examiner—E. H. Eickholt
Attorney, Agent, or Firm—William W. Jones

[57] ABSTRACT

A holder for clamping in place a catheter or other hollow tube, such as a urinary catheter tube, a nasogastric tube or intravenous tube on a patient's body, which holder includes a pliant adhesive-bearing base which is adhered to the patient's skin. The holder is adjustable so as to be capable of holding the catheter tube against rotary and longitudinal movement, and also be capable of partially or completely closing the bore of the catheter tube by deforming the tube wall.

10 Claims, 5 Drawing Figures

CATHETER CLAMP

This invention relates to a holder for securement to the body of a patient for the purpose of properly holding a urinary catheter, nasogastric or intravenous tube in place. The various tubes with which the holder may be used will hereinafter be referred to as "catheter tubes" for convenience. The holder is particularly useful for positioning a urinary catheter tube on a patient, or other similar catheter tube which, if pulled longitudinally or rotationally, can cause the patient discomfort or pain as well as physical trauma and dislodgement of the tube.

Various types of catheter tube holders have been proposed by those skilled in the art. Presently in use are arrangements ranging from the simple tape wrapped around a patient's limb over the catheter tube to hold it in place, to more sophisticated holders of the type disclosed in U.S. Pat. Nos. 3,990,454 and 2,590,006. The rigged tape arrangements have obvious drawbacks in that they are irritating to a patient, time consuming to apply and remove, and do not always hold the catheter tube properly in place. The adhesive portion of the tape may also cause physical-chemical degeneration of the catheter tube. The tapes further may be contaminated with excrement, blood or other body fluid and cannot be easily cleaned. The various other catheter tube holders proposed are generally rather specialized in function and may not always be generally useful in holding a variety of different catheter tubes in place.

This holder is of the general known type of catheter holder which includes a pliant adhesive-bearing base which is much like the flat head of a rubber suction dart or suction cup. This type of catheter holder is shown in the patents referred to above. Attached to and preferably integral with the soft base part of the holder is an externally threaded post which extends perpendicularly to the plane of the base. A pair of articulated jaws are mounted on the threaded post, the jaws including a hinge and a pair of opposed channel-shaped portions which cooperate to form the part of the clamp which engages the catheter tube. A nut is threaded onto the post for adjusting the clamping force which is exerted on the catheter tube.

It is, therefore, an object of this invention to provide a catheter tube holder which has an adhesively-coated pliable base for securement to a patient's body, and which has an adjustable catheter tube-engaging portion connected to the base.

It is a further object of this invention to provide a catheter tube holder of the character described which can be, except for adhesive and paper shield, entirely inexpensively formed from molded plastic and can be thrown away after use.

It is an additional object of this invention to provide a catheter tube holder of the character described wherein the catheter tube-engaging portion is adjustable sufficiently to vary the clamping force exerted on the catheter tube.

These and other objects and advantages of this invention will become more readily apparent from the following detailed description of a preferred embodiment of the catheter holder of this invention taken in conjunction with the accompanying drawings, in which.

Figure 1:
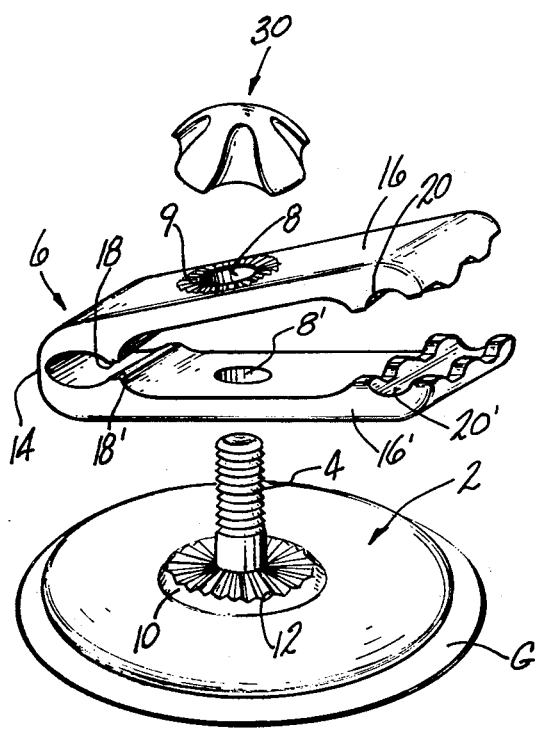
FIG. 1 is an exploded perspective view of a preferred embodiment of a catheter tube holder formed in accordance with the invention.
Figure 3:
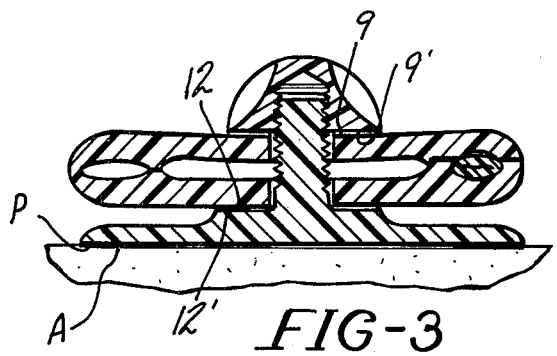
FIG. 3 is a sectional view similar to FIG. 2 wherein the holder is shown engaging the catheter tube to a degree sufficient to block fluid flow through the catheter tube.
Figure 2:
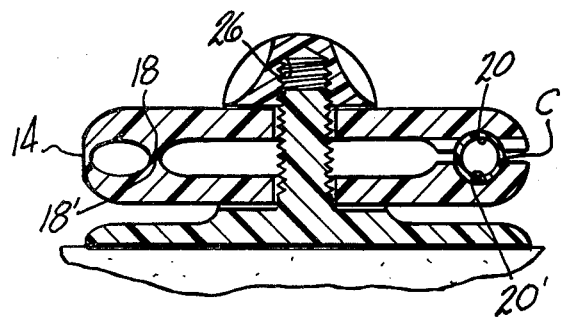
FIG. 2 is a vertical sectional view of the holder of FIG. 1 shown engaging a catheter tube sufficiently to retain the latter against longitudinal and rotary movement.
Figure 4:
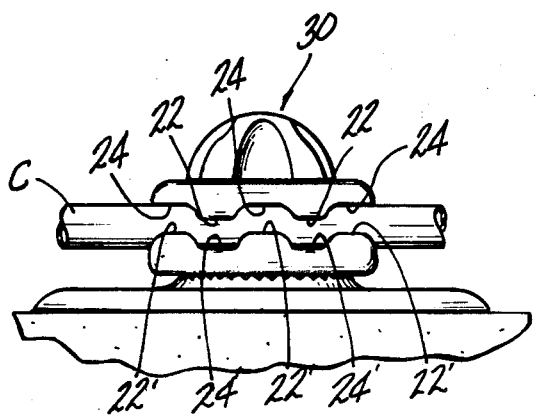
FIG. 4 is a right side elevational view of the holder shown holding a catheter tube clamped in place but not closed against fluid flow.

Referring now to the drawings, there is shown a preferred embodiment of a catheter tube holder formed in accordance with this invention. The holder includes a circular base portion 2 made from a plastic such as nylon, which, when thin enough, is pliant and which can be formed by injection molding. An externally threaded post 4 is preferably made integral with the base 2, as shown in FIGS. 2 and 3. The post 4 is made relatively rigid compared to the base 2 by being thicker in cross section than the base 2. If desired, the post 4 may be made as a separate member of a different plastic or metal, and may be embedded in the base 2 projecting upwardly therefrom. A preferably one-piece jaw member 6 is mounted for preliminary rotation on the post 4, the latter passing through aligned oversized holes 8 and 8' in the member 6, and the member 6 resting upon a flat upper boss 10 formed on the base 2. The top of the boss 10 is formed with radiating splines 12 which match complimentary radiating splines 12' formed in the lower surface of the jaw member 6 about the hole 8'. The member 6 is formed with a transverse strap-type hinge 14 at one end thereof about which upper and lower jaws 16 and 16' are pivoted. Inwardly spaced from the strap hinge 14 is positioned a contact formed by transverse upper and lower ribs 18 and 18'. At the other end of the member 6 there is formed a transverse channel made up of substantially semi-circular upper and lower halves 20 and 20' respectively. The channel forms the catheter tube-receiving clamp. The channel has formed along each of its opposite transverse edges a plurality of extending teeth 22 and 22' spaced apart by recesses 24 and 24'. It will be noted from FIGS. 4 and 5 that the teeth 22 and 22' on each side of the channel are opposite the recesses 24 and 24' on the other side of the channel. It will be noted from FIG. 1 that, preferably, the jaw member 6 is molded in a partially opened position so that the strap hinge 14 will be stressed when the jaw member 6 is pressed closed.

A nut 30 is threaded onto the post 4 and is used to adjust the grip of the clamp. The nut 30 is preferably dome-shaped, with enlarged flutes for manual gripping, and includes a blind threaded bore 26. The nut 30 may be formed from molded plastic, in which case the threads in the bore 26 will be partial threads, or the nut may be formed from metal. The dome shape of the nut 30 eliminates sharp edges or corners which can irritate or cut a patient. As shown in FIG. 2, the catheter tube C is held between the channels 20 and 20' tightly enough so that the catheter tube C cannot move longitudinally of the clamp. When the jaw member 6 is adjusted to the position shown in FIG. 2, the ribs 18 and 18' will be brought into engagement with each other, and the strap hinge 14 will be stressed. Since the ribs 18 and 18' engage on one side of the post 4 and the catheter tube C is clamped in place between the jaws 16 and 16', the pressure exerted by the nut 30 on the upper surface of the jaw member 6 will be transferred, by the ribs 18 and 18' and the catheter tube C, to the lower surface of the jaw member 6 so that the splines 12 and 12' are forced together to lock the jaw member 6 to the base 2 whereby the jaw member 6 can no longer rotate relative to the base 2. In the position shown in FIG. 2, the catheter tube will be held against longitudinal movement in the jaws, and the jaw member 6 will be unable to rotate, therefore, the catheter tube will not exert transmitted force on the portal of entry to the patient's body when the patient moves about in such a way that the catheter tube will be pulled at any location not between the holder and the point of entry of the catheter into the patient. Thus, the provision of a clamp which holds the catheter tube against longitudinal movement greatly increases the comfort and safety of the patient and permits the patient to move about with less painful discomfort which otherwise results from pulling on the catheter tube. To prevent the nut 30 from accidentally loosening, matching radial splines 9 and 9' are formed on the upper surface of the jaw 16 about the hole 8, and on the adjacent lower surface of the nut 30, respectively, as shown in FIGS. 1 and 3.

For adhering the holder to the patient, the lower surface of the base 2 is provided with a porous layer P coated with layer of adhesive A. A protective sheet of adhesive guard G is removably disposed over the adhesive layer A. The holder is secured to the patient, for example to the patient's thigh in the case of a urinary catheter. The catheter tube C is then brought laterally between the channel surfaces 20 and 20' which are sprung open as previously described and the nut 30 is tightened down to the position shown in FIG. 2. It will be noted that the jaw member 6 will swivel about the post 4 until the nut 30 is tightened, so that no particular orientation of the holder need be maintained when the holder is adhered to the patient. When the catheter tube C is secured to the holder, the attendant, i.e., nurse or doctor, will provide sufficient slack between the holder and the point of entry of the catheter into the patient to ensure that movement of the patient which results in movement of the holder will not cause the tube to pull on the point of entry into the patient's body. At the same time, any pulling on the tube which occurs on the side of the holder away from the catheter's point of entry, for any reason whatever, will not result in the catheter being pulled, because the holder prevents such a result.

Figure 5:
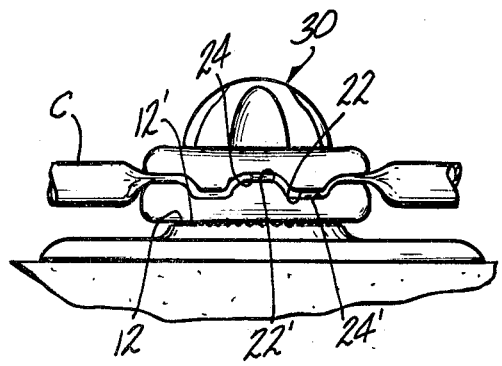
FIG. 5 is a right side view similar to FIG. 4, but showing how the clamp operates to close the catheter tube against fluid flow.

In the event that it is desirable to close off the catheter tube C to, for example, allow emptying of a urine receptacle, the nut 30 is merely tightened down on the post 4, as shown in FIG. 3. This meshes teeth 22, 22' and 24 and 24', as seen in FIG. 5, thereby squeezing the tube C shut. When desired, the tube can be reopened merely by loosening the nut 30 once more to the position shown in FIG. 2, such reopening resulting from relaxation of the strap hinge 14 and re-expansion of the catheter tube C. It will also be apparent that the tube C can also be only partially occluded by the clamp so that flow rate of fluid through the tube can be controlled by the clamp. Because of the threaded post and nut, the degree of occlusion of the tube which can be achieved is substantially infinite.

It will be readily appreciated that the catheter tube holder of this invention can be inexpensively produced and is adaptable to hold a variety of different catheter tube sizes. It can be quickly and easily secured to and removed from the body of the patient, and easily fitted to the catheter tube. The holder prevents the patient from experiencing discomfort when the tube is pulled downstream of the holder by reason of patient movement, and further provides means whereby the tube may be closed off temporarily during treatment or care of the patient.

Since many changes and variations of the disclosed embodiment of the invention may be made without departing from the inventive concept, it is not intended to limit the invention otherwise than as required by the appended claims.

What is claimed is:

1. A catheter tube holder comprising:
   (a) adhesive-coated base means for securing the holder to the skin of a patient;
   (b) jaw means mounted on said base means for free rotational movement with respect to said base means, said jaw means being operable to receive a catheter tube;
   (c) adjustment means for acting upon said jaw means to cause the latter to grip the catheter tube with a clamping action to prevent the catheter tube from moving longitudinally with respect to said jaw means; and
   (d) locking means responsive to actuation of said adjustment means to lock said jaw means against rotation with respect to said base means when the catheter tube is clamped by said jaw means.

2. The holder of claim 1, wherein said adjustment means is further selectively operable to cause said jaw means to squeeze the catheter tube to lessen the rate of fluid flow through the bore of the catheter tube.

3. A catheter tube holder comprising:
   (a) adhesive-coated base means for securing the holder to the skin of a patient;
   (b) a threaded post secured to said base means and extending upwardly therefrom;
   (c) jaw means mounted on said post for free rotation thereabout, said jaw means being operable to receive a catheter tube; and
   (d) an adjustment nut threaded onto said post and operable to be tightened against said jaw means sufficiently to close the latter sufficiently to clamp the catheter tube against longitudinal movement with respect to said jaw means.

4. The holder of claim 3, further comprising cooperating locking means on said base means and said jaw means responsive to tightening action of said nut to lock said jaw means against rotational movement with respect to said base means when the catheter tube is clamped in said jaw means.

5. The holder of claim 3, wherein said jaw means is a one-piece molded plastic body having upper and lower parts interconnected by a strap-type hinge, said upper and lower parts each providing one-half of the part of said jaw means which clamps the catheter tube in place, and said hinge being stressed when said jaw means is clamping the catheter tube in place by reason of said body being molded in an open configuration.

6. The holder of claim 3, wherein said jaw means includes intermeshing teeth formed on opposite parts of said jaw means, said teeth providing means for allowing closure of said jaw means to a degree which will squeeze shut the bore of a catheter tube clamped in said jaw means.

7. A catheter tube holder comprising:

(a) adhesive-coated base means for securing the holder to the skin of a patient;
(b) a threaded post secured to said base means and extending upwardly therefrom;
(c) a one-piece jaw member mounted on said post for rotational movement thereabout, said jaw member including upper and lower halves forming a recess for reception of a catheter tube, said recess being open on one side so that the catheter tube can be moved laterally into said recess, said upper and lower halves being interconnected by integral hinge means for permitting articulated movement of one of said halves with respect to the other of said halves;
(d) an adjustment nut threaded onto said post, said adjustment nut being tightenable against said jaw member to close said recess sufficiently to clamp the catheter tube in said recess against movement with respect to said jaw member; and
(e) locking means on said jaw member and said base means operable in response to tightening of said nut to lock said jaw member against rotational movement with respect to said base means.

8. The holder of claim 7, wherein said integral hinge means is operable to bias said upper and lower halves away from each other to open said recess laterally when said adjustment nut is not tightened against said jaw member.

9. The holder of claim 7, wherein said adjustment nut can be tightened against said jaw member to close said recess sufficiently to squeeze the catheter tube bore closed against fluid flow therethrough.

10. A catheter tube holder comprising:
(a) adhesive-coated base means for securing the holder to the skin of a patient;
(b) jaw means movably mounted on said base means, said jaw means providing first and second parts interconnected by an articulation hinge, and forming a tubular gripping means for receiving a catheter tube, said gripping means being adjustable between an open condition wherein the catheter tube may be moved into and out of said gripping means in a direction normal to the axis of the catheter tube, and a closed condition wherein said gripping means is operable to hold the catheter tube in a fixed position with a clamping action;
(c) adjustment means for closing said gripping means;
(d) means for biasing said gripping means toward its open condition; and
(e) releasable locking means for locking said jaw means against movement relative to said base means.

* * * * *